United States Patent
Wakimasu et al.

(10) Patent No.: US 6,610,655 B2
(45) Date of Patent: *Aug. 26, 2003

(54) PENTAPEPTIDE WITH SPECIFIC CONFORMATION, ITS PRODUCTION AND USE

(75) Inventors: Mitsuhiro Wakimasu, Ibaraki (JP); Hiroshi Inooka, Ibaraki (JP); Satoshi Endo, Osaka (JP); Takashi Kikuchi, Ibaraki (JP)

(73) Assignee: Takeda Chemical Industries, Inc. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/999,432

(22) Filed: Nov. 15, 2001

(65) Prior Publication Data

US 2002/0115823 A1 Aug. 22, 2002

Related U.S. Application Data

(63) Continuation of application No. 08/969,007, filed on Nov. 12, 1997, now Pat. No. 6,346,604, which is a division of application No. 08/551,251, filed on Oct. 31, 1995, now Pat. No. 5,965,526, which is a continuation of application No. 08/180,922, filed on Jan. 13, 1994, now abandoned.

(51) Int. Cl.[7] ............................ C07K 1/02; C07K 1/10; C07K 1/113
(52) U.S. Cl. ............................ 514/11; 514/9; 530/333; 530/335; 530/338
(58) Field of Search ................................ 530/333, 335, 530/338; 514/11, 9

(56) References Cited

U.S. PATENT DOCUMENTS 6,346,604 B1 * 2/2002 Wakimasu et al. .......... 530/333

OTHER PUBLICATIONS

Rudinger, J. Peptide Hormones (ed. J.A. Parsons: University Park Press Jun. 1976) pp. 1–6.*
Krystek et al., FEBS vol. 299, No. 3 pp. 255–261 (Mar. 1992).*
Nakajima et al., J. Antibiotics vol. 44(12) (Dec. 1991) pp. 1348–1356.*

* cited by examiner

Primary Examiner—Bennett M Celsa
(74) Attorney, Agent, or Firm—Edwards & Angell, LLP; David G. Conlin; Cara Z. Lowen

(57) ABSTRACT

Cyclic pentapeptides are disclosed having the following formula (I)-Cyclo(-$A_1$-$A_2$-$A_3$-$A_4$-$A_5$-)-wherein $A_1$, $A_2$, $A_3$, $A_4$ and $A_5$ are amino acid residues. The pentapeptide has amino acid residues in positions 1-2-3 to form a γ-turn, and amino acid residues in positions 3-4-5-1 to form a β-turn in combination with the γ-turn. D-α-amino acid residues are selected for $A_1$, $A_3$, and $A_5$ and L-α-amino acid residues are selected for $A_2$ and $A_4$. Compounds having γ-turns and β-turns can be synthesized, regardless of the kinds of amino acid residues, and it is possible to synthesize compounds in which desired amino acid residues are introduced into sites of β-turn and γ-turn based on their importance from the viewpoint of biological activity. The present invention is therefore available for design of compounds having biological activity.

1 Claim, 10 Drawing Sheets c(-D-Glu-Ala-D-Phe-Leu-D-Trp)

| | 1 | 2 | 3 | 4 | 5 |
|---|---|---|---|---|---|
| Residue | D-Glu | L-Ala | D-Phe | L-Leu | D-Trp |
| $J_{N\alpha}$(Hz) | 7.5 | 7.7 | 9.2 | 6.9 | 8.2 |

$d_{NN}$ $d_{\alpha N}$ $d_{\alpha N}(i, i+2)$

| $\delta NH/T$ ($\times 10^{-3}$ ppm/°C) | -2.3 | -7.9 | -3.2 | -6.6 | -8.6 |
|---|---|---|---|---|---|

FIG. 3 cyclo(-D-Glu-Ala-D-Leu-Leu-D-Trp-)

expectation

Retro-inverso form cyclo(-Trp-D-Leu-Leu-D-Ala-Glu-)

PENTAPEPTIDE WITH SPECIFIC CONFORMATION, ITS PRODUCTION AND USE

This application is a continuation application of application Ser. No. 08/969,007, filed Nov. 12, 1997, now U.S. Pat. No. 6,346,604, which is a divisional of application Ser. No. 08/551,251, filed Oct. 31, 1995, issued as U.S. Pat. No. 5,965,526, on Oct. 12, 1999, which was a continuation of application Ser. No. 08/180,922, filed on Jan. 13, 1994, abandoned.

FIELD OF THE INVENTION

The present invention relates to a novel method for producing a cyclic pentapeptide having a β-turn and a γ-turn, cyclic pentapetides having a β-turn and a γ-turn and use thereof.

PRIOR ART

The β-turn and the γ-turn are known as one of regular structures of proteins or peptide molecules, and have structures bending at 4- and 3-amino acid residues, respectively. Usually, the β-turn forms a hydrogen bond between carbonyl oxygen in the i-position and an amide proton in the i+3-position, and is classified into type I and type II according to two dihedral angles φ and ψ of the i+1-position and the i+2-position. The γ-turn forms a hydrogen bond between the i-position and the i+2-position. Such turn structures relates to intermolecular recognition and molecular interaction in many cases, because of their projected structures from molecular surfaces. With recent developments of X-ray crystal structure analysis and NMR analysis, three-dimensional structures of many biologically active peptides have been determined. Examples of peptides containing β-turns in active sites include enkephalin [T. S. Sudha & P. Balaram, *Int. J. Pept. Protein Res.*, 21(4), 381–388 (1983), and M. Goodman et al., *Biopolymers*, 26 (Supp.), S25–S32 (1987)] and somatostatin [U. Nagai et al., *Pept.: Chem. Biol., Proc. Am. Pept. Symp.* 10th, 129–130 (1988)]. Attempts have further been made to imitate the β-turn portions with non-peptide compounds [J. B. Ball & P. F. Alewood, *J. Mol. Recognit.*, 3(2, 55–64 (1990), and G. L. Olson et al., *J. Am. Chem. Soc.*, 112(1), 323–333 (1990)]. It has also been reported that RGD(Arg-Gly-Asp)-related peptides having vitronectin-sensitive cell adhesion activity have γ-turns in adhesion sites [G. Muler et al., *Angew. Chem. Int. Ed. Engl.*, 31(3), 326–328 (1992)]. Recently, cyclic pentapeptide BQ123 was reported as an antagonist against endothelin by Banyu Pharmaceutical Co., Ltd. (U.S. Pat. No. 5,114,918) but it does not describe its conformation. Further, a specific cyclic pentapeptide as an endothelin receptor-antagonist or as an endothelin-antagonist, respectively has been reported to have a β-turn and a γ-turn [R. A. Atkinson & J. T. Pelton, *FEBS Lett.*, 296(1), 1–6 (1992), and S. R. Krystek Jr. et al., FEBS Lett., 299(3), 255–261 (1992)]. This is considered to be a three-dimensional structure inherent in the specific amino acid sequence of that specific cyclic pentapeptide.

SUMMARY OF THE INVENTION

A method for synthesizing peptides having a β-turn followed by a γ-turn or a γ-turn followed by a β-turn, can contribute to the development of drugs. Further, methods for introducing desired amino acid residues into the sites for the β- and γ-turns can facilitate effective designing of compounds having biological activity.

The present inventors synthesized various cyclic pentapeptides and conducted intensive investigations of the conformations thereof. As a result, the present inventors discovered a novel manufacturing method by which compounds having β- and γ-turns could be synthesized at will, regardless of residues.

The present invention directs to a novel method for forming β- and γ-turns, only by controlling optical activity of a main chain of a cyclic pentapeptide, regardless of the kind of residues, a cyclic pentapeptide having β- and γ-turns and use thereof.

Namely, the present invention provides (1) A cyclic pentapeptide having a γ-turn and a β-turn wherein the cyclic pentapeptide has the following formula (I):

Cyclo(-A$_1$-A$_2$-A$_3$-A$_4$-A$_5$-)     (I)

wherein A$_1$, A$_2$, A$_3$, A$_4$ and A$_5$ are amino acid residues; said pentapeptide comprising amino acid residues in positions 1-2-3 to form a γ-turn, and amino acid residues in positions 3-4-5-1 to form a β-turn in combination with the γ-turn;
in which D-α-amino acid residues are selected for A$_1$, A$_3$ and A$_5$ and L-α-amino acid residues are selected for A$_2$ and A$_4$ or L-α-amino acid residues are selected for A$_1$, A$_3$ and A$_5$ and D-α-amino acid residues are selected for A$_2$ and A$_4$;
(2) the cyclic pentapeptide of (1), in which A$_1$, A$_3$ and A$_5$ are D-α-amino acid residues, and A$_2$ and A$_4$ are L-α-amino acid residues, with the proviso that when A$_1$ is D-Asp, A$_3$ is D-Val, A$_4$ is L-Leu and A$_5$ is D-Trp, A$_2$ is L-amino acid other than L-Pro; (3) the cyclic pentapeptide of (2), in which A$_1$ is D-alanine, D-valine, D-norvaline, D-leucine, D-norleucine, D-isoleucine, D-alloisoleucine, D-phenylalanine, D-tyrosine, D-tryptophan, D-serine, D-threonine, D-ornithine, D-lysine, D-arginine, D-histidine or D-methionine; A$_2$ is an L-α-amino acid; A$_3$ is a D-α-amino acid; A$_4$ is an L-α-amino acid; and A$_5$ is D-α-amino acid; (4) the cyclic pentapeptide of (2), in which A$_1$ is D-aspartic acid, D-glutamic acid or D-cysteic acid; A$_2$ is an L-α-amino acid; A$_3$ is a D-α-amino acid; A$_4$ is an L-α-amino acid; and A$_5$ is D-valine, D-norvaline, D-leucine, D-norleucine, D-isoleucine, D-alloisoleucine, D-serine, D-threonine, D-aspartic acid, D-glutamic acid, D-ornithine, D-lysine, D-arginine, D-histidine, D-methionine or D-cysteine; (5) the cyclic pentapeptide of (2), in which A$_1$ is D-aspartic acid, D-glutamic acid or D-cysteic acid; A$_2$ is an L-α-amino acid; A$_3$ is D-phenylalanine, D-tyrosine, D-tryptophan, D-serine, D-aspartic acid, D-glutamic acid, D-ornithine, D-lysine, D-arginine, D-histidine, D-methionine or D-cysteine; A$_4$ is an L-α-amino acid; and A$_5$ is D-phenylalanine, D-tyrosine, D-alanine or D-tryptophan; (6) the cyclic pentapeptide of (1), in which A$_1$, A$_3$ and A$_5$ are L-α-amino acid residues, and A$_2$ and A$_4$ are D-α-amino acid residues; (7) the cyclic pentapeptide of (1), in which A$_1$ is a D-α-amino acid; A$_2$ is an L-α-amino acid having a protective group for the amino acid; A$_3$ is a D-α-amino acid; A$_4$ is an L-α-amino acid; and A$_5$ is a D-α-amino acid; (8) the cyclic pentapeptide of (7), in which a protective group is hydrophobic; (9) the cyclic pentapeptide of (8), in which a protective group is benzyl; (10) the cyclic pentapeptide of (7) is cyclo(-D-Glu-Ser(Bzl)-D-Leu-Leu-D-Trp); (11) the cyclic pentapeptide of (7) is cyclo(-D-Glu-Thr(Bzl)-D-Leu- Leu-D-Trp); (12) an NK2 receptor antagonist composition comprising any one of the cyclic pentapeptides of (1) to (11) and pharmaceutically acceptable carrier; (13) the composition of (12), in which said antagonist is an antiasthmatic agent, an anti-inflammatory agent or an antarthritic agent; (14) a method for producing a cyclic pentapeptide having a γ-turn and a β-turn wherein the cyclic pentapeptide has the following formula (I):

 (I)

wherein $A_1$, $A_2$, $A_3$, $A_4$ and $A_5$ are amino acid residues; said method comprising selecting and reacting amino acid residues in positions 1-2-3 to form a γ-turn, and selecting and reacting amino acid residues in positions 3-4-5-1 to form a β-turn in combination with the γ-turn; in which D-α-amino acid residues are selected for $A_1$, $A_3$ and $A_5$ and L-α-amino acid residues are selected for $A_2$ and $A_4$ or L-α-amino acid residues are selected for $A_1$, $A_3$ and $A_5$ and D-α-amino acid residues are selected for $A_2$ and $A_4$; (15) the method of (14), further comprising condensing two kinds of fragments to form a linear pentapeptide, and then cyclizing resulting linear pentapeptide to form the cyclic pentapeptide; and (16) a method of treating mammalian asthma, inflammation or arthritis which comprises administering to said mammal a pharmaceutical composition comprising an effective amount of any one of the cyclic pentapeptides of claim 1 to 11.

BRIEF DESCRIPTION OF THE DRAWINGS

FIG. 3 shows a diagram summarizing NMR information of cyclic pentapeptide (A).

$J_N\alpha$ indicates a coupling constant value between an amide proton and an α-proton, and $d_{NN}$ and $d\alpha_N$ indicate NOE connectivities between the ith amide proton and α-proton and the (i+1)th amide proton, respectively. $d\alpha_N$ (i, i+2) indicates an NOE connectivities between the ith α-proton and the (i+2)th amide proton. $\delta_{NH}/T$ indicates temperature dependence of a chemical shift of an amide proton.

Figure 4:
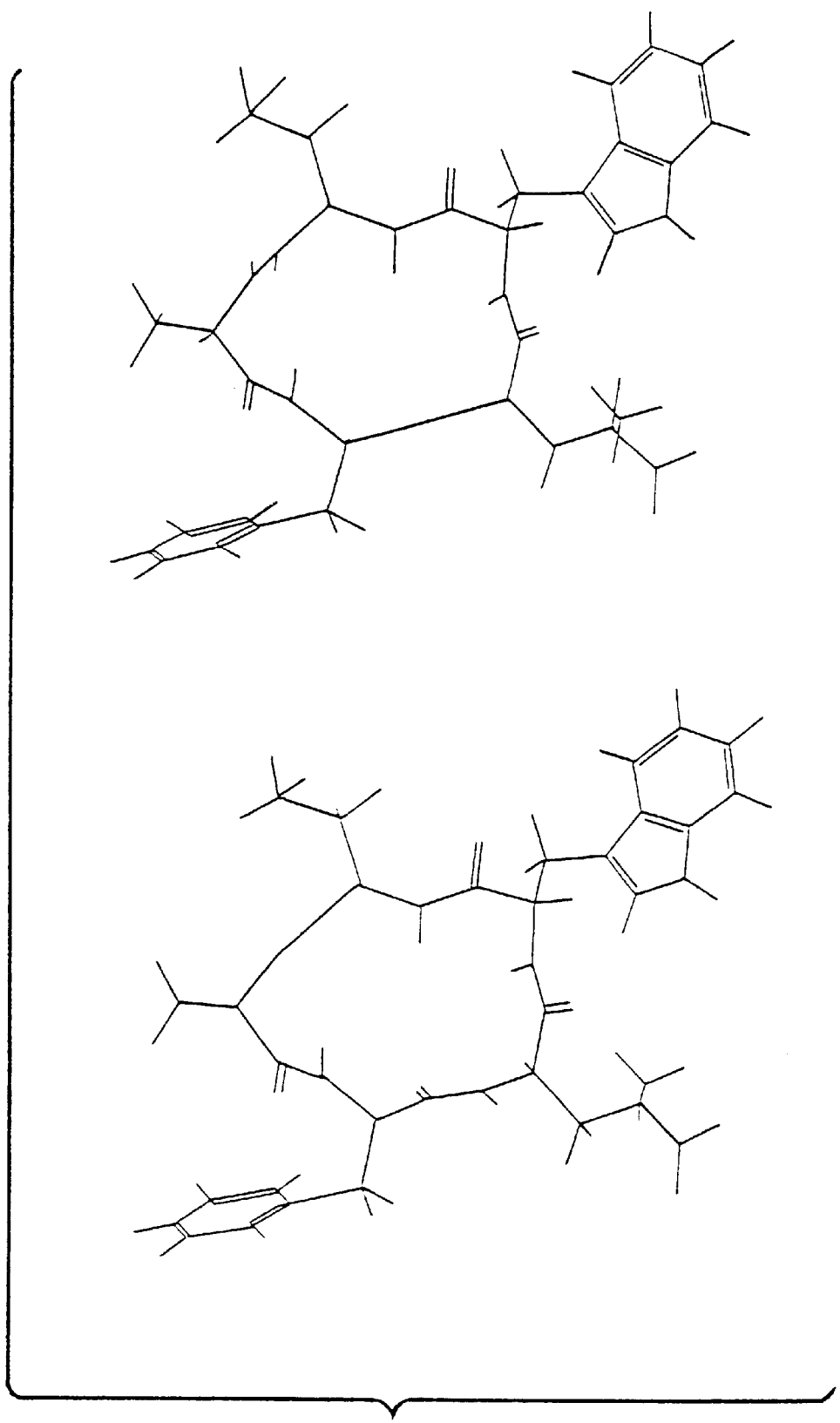

FIG. 4 shows a stereoview of the three-dimensional structure of (A) determined by calculation based on distance information obtained from NMR.

Figure 5:
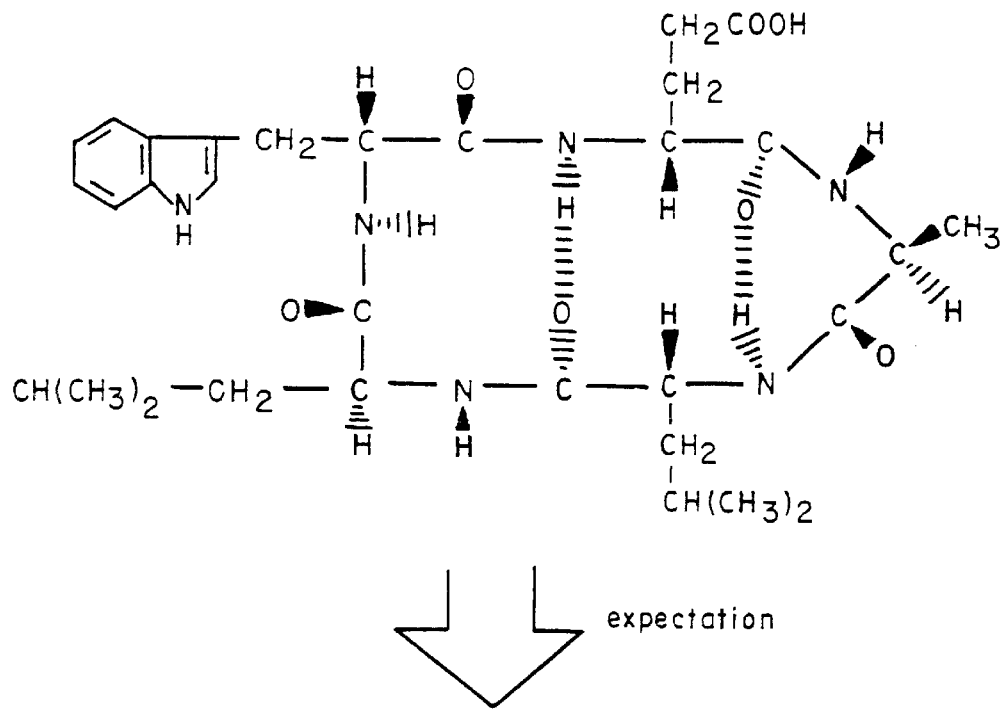
Figure 5:
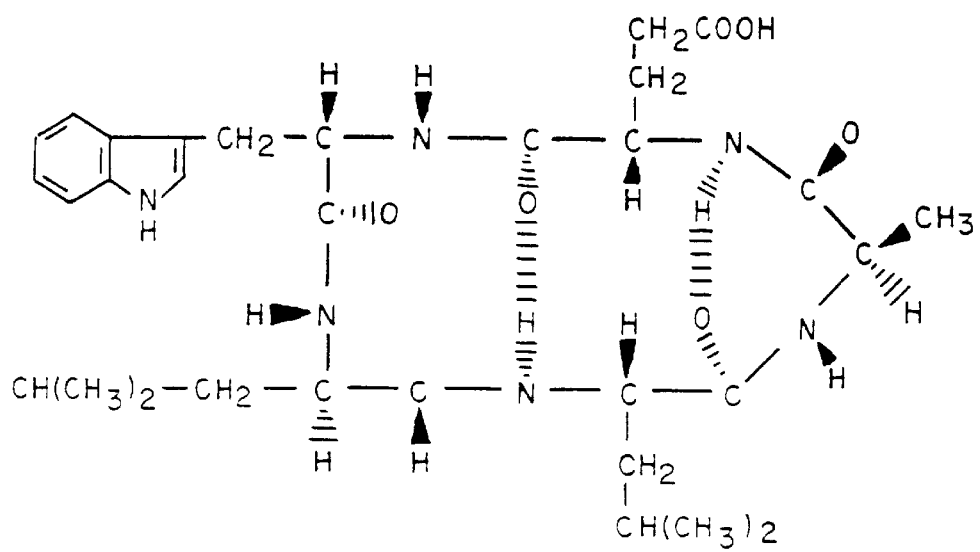

FIG. 5 is schematic views showing the three-dimensional structure of cyclic pentapeptide cyclo(-D-Glu-Ala-D-Leu-Leu-D-Trp-) and the expected three-dimensional structure of retro-inverso form (B) designed on the basis thereof.

Figure 6:
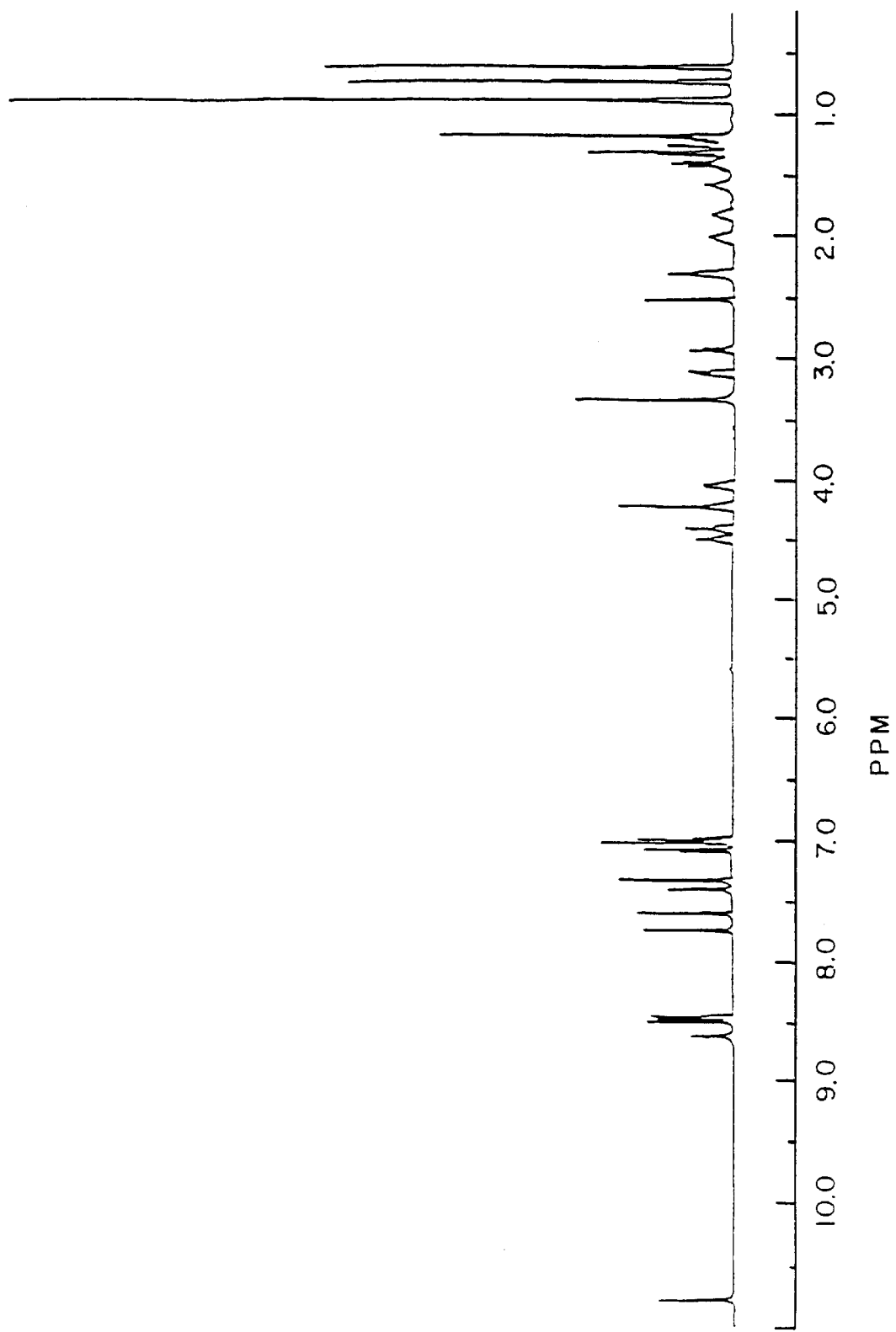

FIG. 6 shows a $^1$H NMR spectrum of cyclic pentapeptide cyclo(-Trp-D-Leu-Leu-D-Ala-Glu-) (B) corresponding to the above-mentioned retro-inverso form.

Figure 7:
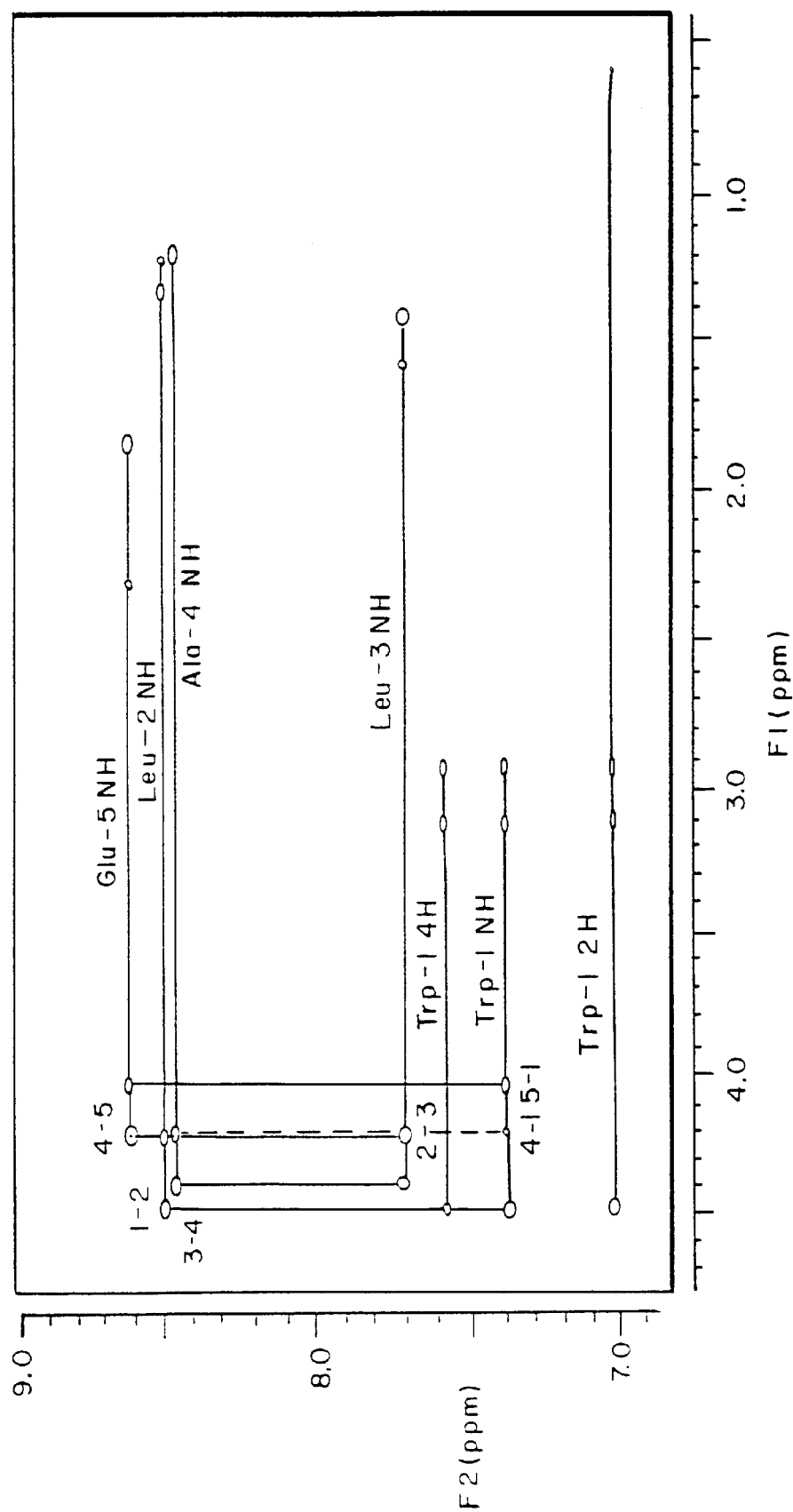

FIG. 7 shows a ROESY spectrum ($\tau_M$=120 ms) of cyclic pentapeptide (B). The horizontal lines and the numerals with hyphens have the same meanings as given in FIG. 4.

Figure 8:
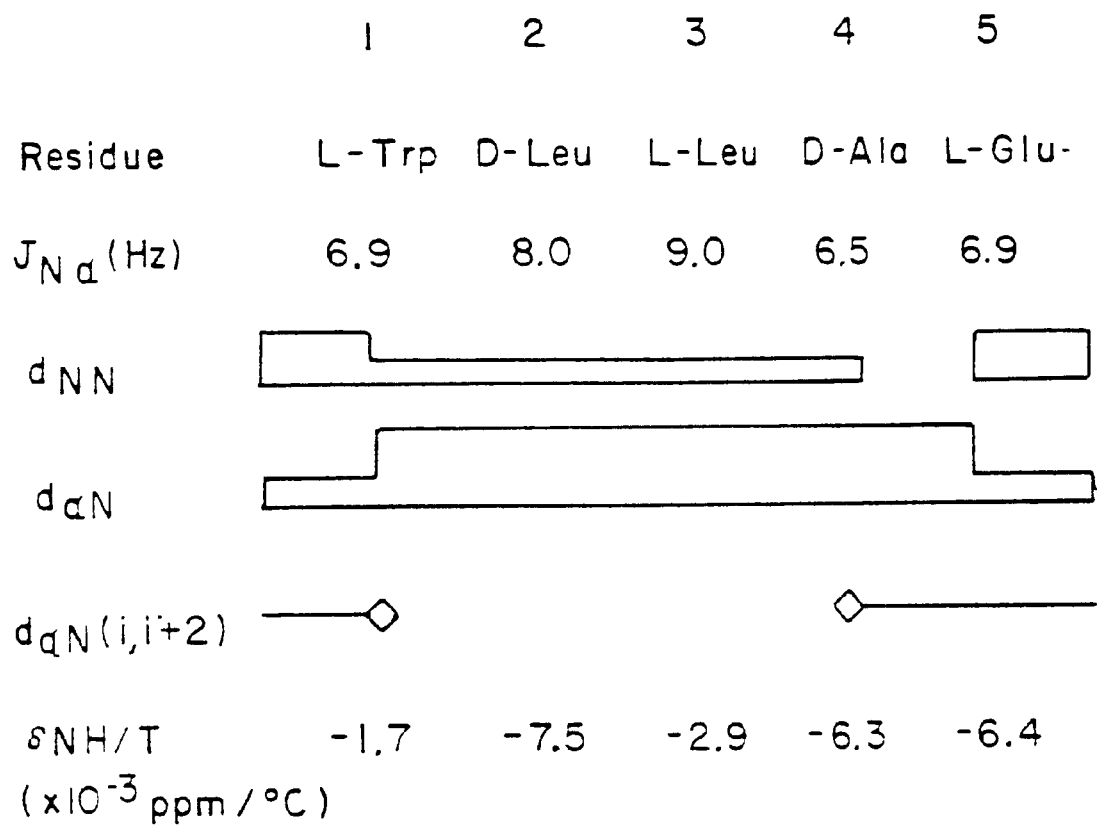

FIG. 8 shows a diagram summarizing NMR information of cyclic pentapeptide (B). The symbols have the same meanings as defined in FIG. 3.

Figure 9:
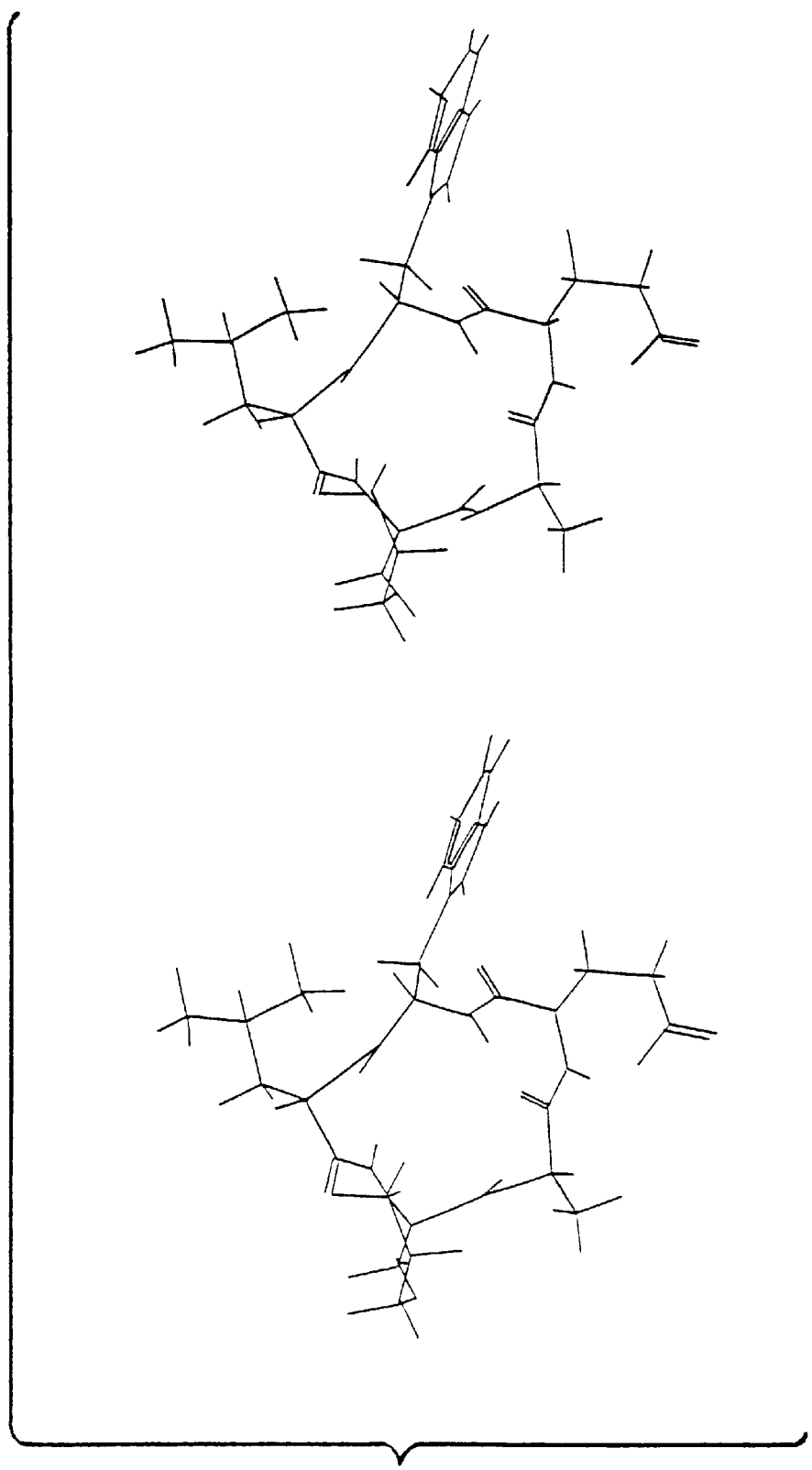

FIG. 9 shows a stereoview of the three-dimensional structure of (B) determined by calculation based on distance information obtained as described above.

Figure 10:
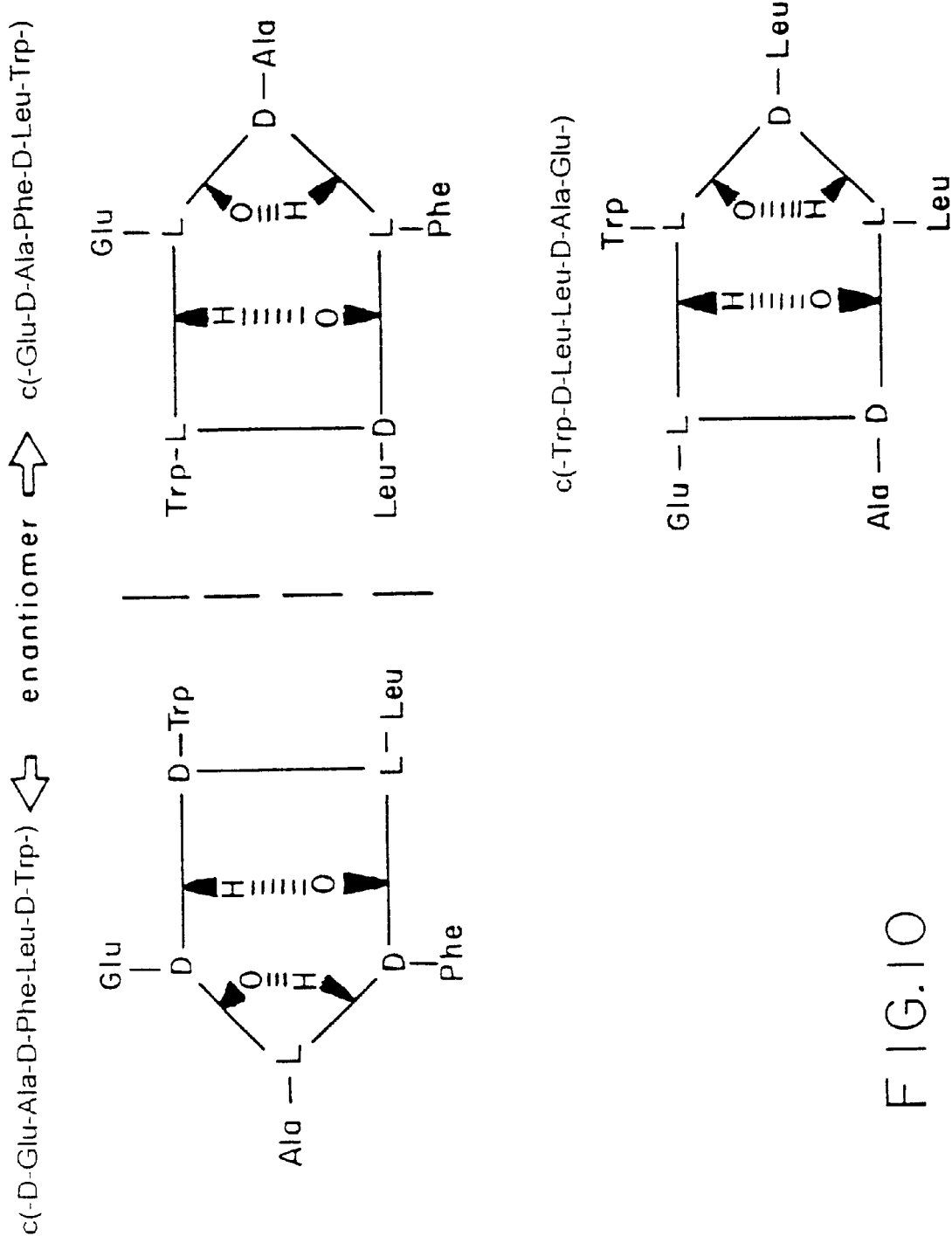

FIG. 10 is schematic views showing that cyclo(-Glu-D-Ala-Phe-D-Leu-Trp-) (A') obtained by exchanging the arrangement of D and L in (A) has the three-dimensional structure corresponding to the enantiomer to (A), and that (B) has the same main chain conformation as (A').

DESCRIPTION OF THE PREFERRED EMBODIMENTS

In the above-mentioned general formula (I), examples of the α-amino acid residues represented by $A_1$, $A_2$, $A_3$, $A_4$ and $A_5$ include alanine, valine, norvaline, leucine, norleucine, isoleucine, alloisoleucine, phenylalanine, tyrosine, tryptophan, serine, threonine, aspartic acid, glutamic acid, ornithine, lysine, arginine, histidine, methionine and cysteine. $A_2$ further includes proline. In addition, a side chain of each amino acid may be substituted. Groups used as substituents of the side chains of the amino acids include protective groups for amino groups, protective groups for thiol groups, protective groups for guanidino groups, protective groups for hydroxyl groups, protective groups for phenolic hydroxyl groups, protective groups for imidazole and protective groups for indole, which are described below.

In this specification, amino acids and peptides are indicated by the abbreviations commonly used in the art or adopted by the IUPAC-IUB Commission on Biochemical Nomenclature. For example, the following abbreviations are used:

| | |
|---|---|
| Gly | Glycine |
| Ala | Alanine |
| Val | Valine |
| Nva | Norvaline |
| Ile | Isoleucine |
| aIle | Alloisoleucine |
| Leu | Leucine |
| tLeu | t-Leucine |
| γMeLeu | γ-Methylleucine |
| Met | Methionine |
| Arg | Arginine |
| Lys | Lysine |
| His | Histidine |
| Asp | Aspartic acid |
| Glu | Glutamic acid |
| Asn | Asparagine |
| Gln | Glutamine |
| Ser | Serine |
| Thr | Threonine |
| Phe | Phenylalanine |
| Tyr | Tyrosine |
| Trp | Tryptophan |
| mTrp | 5-Methyltryptophan |
| Phg | Phenylglycine |
| Nal (1) | 1-Naphthylalanine |
| Nal (2) | 2-Naphthylalanine |

Protective groups and reagents commonly used in this specification are indicated by the following abbreviations:

| | |
|---|---|
| Boc | t-Butoxycarbonyl |
| Bzl | Benzyl |
| BrZ | 2-Bromobenzyloxycarbonyl |
| ClZ | 2-Chlorobenzyloxycarbonyl |
| Tos | p-Toluenesulfonyl |
| For | Formyl |
| OBzl | Benzyl ester |
| OPac | Phenacyl ester |
| ONB | HONB ester |
| TFA | Trifluoroacetic acid |

| | |
|---|---|
| TEA | Triethylamine |
| IBCF | Isobutyl chloroformate |
| DMF | N,N-Dimethylformamide |
| DCC | N,N'-Dicyclohexylcarbodiimide |
| DCU | N,N'-Dicyclohexylurea |
| HONB | N-Hydroxy-5-norbornene-2,3-dicarboxyimide |
| HOBt | 1-Hydroxybenzotriazole |
| DCM | Dichloromethane |
| THF | Tetrahydrofuran |
| DMSO | Dimethyl sulfoxide |

The cyclic pentapeptides according to the present invention represented by formula [I] can be produced by known methods for peptide synthesis, which may be either solid phase synthesis methods or liquid phase synthesis methods. In some cases, the liquid phase synthesis methods are preferred. Examples of such methods for peptide synthesis include methods described in M. Bodansky and M. A. Ondetti, *Peptide Synthesis,* Interscience, New York (1966); F. M. Finn and K. Hofmann, *The Proteins,* Vol. 2, edited by H. Neurath and R. L. Hill, Academic Press, New York, (1976); N. Izumiya et al., *Peptide Gosei no Kiso to Jikken* (*Fundamentals and Experiments of Peptide Synthesis*), Maruzen (1985); H. Yazima, S. Sakakibara et al., *Seikagaku Jikken Koza* (*Course of Biochemical Experiments*), 1, edited by Biochemical Society of Japan, Tokyo Kagaku Dojin (1977); H. Kimura et al., *Zoku Seikagaku Jikken Koza* (*Course of Biochemical Experiments, second series*), 2, edited by Biochemical Society of Japan, Tokyo Kagaku Dojin (1987); and J. M. Stewart and J. D. Young, *Solid Phase Peptide Synthesis,* Pierce Chemical Company, Illinois (1984), which describe azide methods, chloride methods, acid anhydride methods, mixed acid anhydride methods, DCC methods, active ester methods, methods using Woodward reagent K, carbodiimidazole methods, oxidation-reduction methods, DCC/HONB methods and methods using BOP [benzotriazole-1-yl-oxy-tris(dimethylamino) phosphonium hexafluorophosphate] reagents.

The cyclic peptide according to the present invention is represented by the following formula (I):

$$\text{Cyclo}(-A_1-A_2-A_3-A_4-A_5-) \quad (I)$$

wherein each of $A_1$, $A_2$, $A_3$, $A_4$ and $A_5$ represents an α-amino acid residue;

said pentapeptide comprising amino acid residues in positions 1-2-3 to form a γ-turn, and amino acid residues in positions 3-4-5-1 to form a β-turn in combination with the γ-turn;

in which D-α-amino acid residues are selected for $A_1$, $A_3$ and $A_5$ and L-α-amino acid residues are selected for $A_2$ and $A_4$ or L-α-amino acid residues are selected for $A_1$, $A_3$ and $A_5$ and D-α-amino acid residues are selected for $A_2$ and $A_4$. Since the present invention refers to cyclic peptides, cyclic permuation of amino acids $A_1$ through $A_5$ in formula (I) represents the same compounds.

The cyclic peptide can be produced by obtaining a linear peptide consisting of five amino acid residues and cyclyzing the resulting linear peptide. The linear peptide may be produced by condensing two or more fragments for the peptide or by condensing amino acids one by one. One fragment having less than 5 amino acid residues of the cyclopeptide and the other fragment comprising the compliment of amino acid residues so that the total is five. One fragment may have one to four amino acid residues.

The cyclo peptide can be produced by activating a carboxyl group of a first starting material corresponding to one of two or more kinds of fragments or an amino group of a second starting material corresponding to the other fragment, protecting functional groups which do not take part in the reaction, condensing both the fragments by methods known in the art to form a linear pentapeptide, subsequently eliminating protective groups of the C-terminal α-carboxyl group and the N-terminal α-amino group of the resulting compound concurrently or stepwise, thereafter conducting intramolecular condensation of the C-terminal α-carboxyl group and the N-terminal α-amino group by ring-closing condensation known in the art such as previously cited references to obtain a cyclic pentapeptide, and then, eliminating protective groups by methods known in the art as so desired, if the resulting condensed product has any protective groups.

Here, a three-dimensional structure in which a γ-turn at positions 1-2-3 in combination with a β-turn at positions 3-4-5-1 can be obtained by selecting D-α-amino acid residues as $A_1$, $A_3$ and $A_5$, and L-α-amino acid residues as $A_2$ and $A_4$, or selecting L-α-amino acid residues as $A_1$, $A_3$ and $A_5$, and D-α-amino acid residues as $A_2$ and $A_4$.

The cyclic pentapeptide produced by the method of the present invention is concretely represented by the following formula (II):

$$\text{Cyclo}(-A_1'-A_2'-A_3'-A_4'-A_5'-) \quad (II)$$

wherein each of $A_1'$, $A_3'$ and $A_5'$ represents a D-α-amino acid residue, and each of $A_2'$ and $A_4'$ represents an L-α-amino acid residue, or each of $A_1'$, $A_3'$ and $A_5'$ represents an L-α-amino acid residue, and each of $A_2'$ and $A_4'$ represents a D-α-amino acid residue. ' in $A_1$ to $A_5$ means inclusion of the protected $A_1$ to $A_5$.

In the above-mentioned formula, as the D-α-amino acid residues represented by $A_1'$, $A_2'^{1}$, $A_3'$, $A_4'$ and $A_5'$, D-forms of the above-mentioned α-amino acid residues represented by $A_1$, $A_2$, $A_3$, $A_4$ and $A_5$ are used, and as the L-α-amino acid residues represented by $A_1'$, $A_2'$, $A_3'$, $A_4'$ and $A_5'$, L-forms of the above-mentioned α-amino acid residues represented by $A_1$, $A_2$, $A_3$, $A_4$ and $A_5$ are used.

Although the present invention will be more concretely illustrated with reference to examples given below, the cyclic pentapeptide represented by formula (II) having the three-dimensional structure in which the γ-turn at positions 1-2-3 in combination with the β-turn at positions 3-4-5-1 can be produced by condensing, for example, a dipeptide X-$A_1'$-$A_2'$-OH with a tripeptide H-$A_3'$-$A_4'$-$A_5'$-Y (wherein each of X and Y represents a protective group; each of $A_1'$, $A_3'$ and $A_5'$ represents a D-α-amino acid residue, and each of $A_2'$ and $A_4'$ represents an L-α-amino acid residue; or each of $A_1'$, $A_3'$ and $A_5'$ represents an L-α-amino acid residue, and each of $A_2'$ and $A_4'$ represents a D-α-amino acid residue) to form a linear pentapeptide represented by H-$A_1'$-$A_2'$-$A_3'$-$A_4'$-$A_5'$-OH, followed by ring-closing condensation.

Protection of functional groups which should not affect the reaction of the starting materials, the protective groups and elimination of the protective groups, and activation of functional groups related to the reaction can also be suitably selected from groups and methods well known to those skilled in the art.

The protective groups for the amino groups constituting the peptides of the present invention represented by formulae (I) and (II) and for the functional groups of the amino acids used as the starting materials are described below.

Examples of the protective groups for the amino groups include carbobenzoxy, t-butyloxycarbonyl, t-amyloxycarbonyl, isobornyloxycarbonyl, 4-methoxybenzyloxycarbonyl, 2-chlorobenzyloxycarbonyl, adamantyloxycarbonyl, trifluoroacetyl, phthalyl, formyl, 2-nitrophenylsulfenyl, diphenylphosphinothioyl and 9-fluorenylmethyloxycarbonyl. The protective groups for the carboxyl groups include, for example, alkyl esters-(such as esters of methyl, ethyl, propyl, butyl, t-butyl, cyclopentyl, cyclohexyl, cycloheptyl, cyclooctyl and 2-adamantyl), benzyl esters, 4-nitrobenzyl esters, 4-methoxybenzyl esters, 4-chlorobenzyl esters, benzhydryl esters, phenacyl esters, benzyloxycarbonylhydrazide, t-butyloxycarbonylhydrazide and tritylhydrazide.

The protective groups for the thiol group of cysteine include, for example, p-methoxybenzyl, 4-methylbenzyl, benzyl, t-butyl, adamantyl, trityl, acetamidomethyl, carbomethoxysulfenyl and 3-nitro-2-pyridinesulfenyl.

The protective groups for the guanidino group of arginine include, for example, nitro, tosyl, p-methoxybenzenesulfonyl, mesitylenesulfonyl, pentamethylbenzenesulfonyl, 4-methoxy-2,3,6-trimethylbenzenesulfonyl, carbobenzoxy, isobornyloxycarbonyl and adamantyloxycarbonyl. The guanidino group may be protected in the form of salts of acids (such as benzenesulfonic acid, hydrochloric acid and sulfuric acid).

The hydroxyl group of serine or threonine can be protected, for example, by esterification or etherification. Examples of groups suitable for this esterification include lower alkanoyl groups such as acetyl, aroyl groups such as benzoyl, and carbonic acid-derived groups such as benzyloxycarbonyl and ethyloxycarbonyl. Examples of groups suitable for the etherification include benzyl, tetrahydropyranyl and t-butyl. However, the hydroxyl group of serine or threonine is not always required to be protected.

Examples of the protective groups for the phenolic hydroxyl group of tyrosine include benzyl, 2,6-dichlorobenzyl, 2-nitrobenzyl, 2-bromobenzyloxycarbonyl and t-butyl. However, the phenolic hydroxyl group of tyrosine is not always required to be protected.

Methionine may be protected in the form of sulfoxides.

The protective groups for the imidazole ring of histidine include p-toluenesulfonyl, 4-methoxy-2,3,6-trimethylbenzenesulfonyl, 2,4-dinitrophenyl, benzyloxymethyl, t-butoxymethyl, t-butoxycarbonyl, trityl and 9-fluorenylmethyloxycarbonyl. However, the imidazole ring is not always required to be protected.

The protective groups for the indole ring of tryptophan include formyl, 2,4,6-trimethylbenzensulfonyl, 2,4,6-trimethoxybenzenesulfonyl, 4-methoxy-2,3,6-trimethylbenzenesulfonyl, β,β,β-trichloroethyloxycarbonyl and diphenylphosphinothioyl-t-butoxycarbonyl. However, the indole ring is not always required to be protected.

The carboxyl group is activated for the above-mentioned condensation reaction and the ring-closing condensation reaction prior to the reaction. Examples of the activated carboxyl groups include the corresponding acid anhydrides, azides and active esters (esters of alcohols such as pentachlorophenol, 2,4,5-trichlorophenol, 2,4-dinitrophenol, cyanomethyl alcohol, p-nitrophenol, N-hydroxy-5-norbornene-2,3-dicarboxyimide, N-hydroxysuccinimide, N-hydroxyphthalimide and N-hydroxybenzotriazole.

The amino group may be activated instead of the carboxyl group. Examples of the activated amino groups include the corresponding phosphoric acid amides.

The condensation reaction can be conducted in the presence of a solvent(s). The solvent(s) can be appropriately selected from the solvents commonly used in peptide condensation reactions. Examples of the solvents include anhydrous or hydrous dimethylformamide, dimethyl sulfoxide, pyridine, chloroform, dioxane, dichloromethane, tetrahydrofuran, acetonitrile, ethyl acetate, N-methylpyrrolidone and appropriate mixtures thereof.

The reaction temperature is appropriately selected from the temperature range commonly used in peptide bond-forming reaction, usually from the range of about −20 to about 30° C.

The intramolecular cyclization reaction can be conducted by methods known in the art. For example, the C-α-carboxyl protective group of the C-terminal amino acid of the protected pentapeptide is first eliminated by methods known in the art, and then, the carboxyl group is activated by methods known in the art, followed by elimination of the N-α-amino protective group of the N-terminal α-amino acid by methods known in the art and intramolecular ring-closing condensation. The C-α-carboxyl protective group of the C-terminal amino acid and the N-α-amino protective groups of the N-terminal amino acid of the protected pentapeptide may be concurrently or in the order eliminated, followed by intramolecular cyclization according to known condensation reaction using a condensing agent such as dicyclohexylcarbodiimide. In some cases, the intramolecular ring-closing condensation reaction is preferably conducted in a highly diluted state.

When the peptide represented by formula (I) produced according to the present invention has a protective group, the protective group can be eliminated in the usual manner. However, the peptide represented by formula (I) having the protective group without elimination also exhibits biological activity.

Examples of methods for eliminating the protective groups include catalytic reduction in the presence of a catalyst such as palladium black or Pd-carbon in a stream of hydrogen, acid treatment with anhydrous hydrogen fluoride, methanesulfonic acid, trifluoromethanesulfonic acid, trifluoroacetic acid or mixtures thereof, and reduction with sodium in liquid ammonia. The elimination reaction by the above-mentioned acid treatment is generally conducted at a suitable temperature between −20 and 40° C. In the acid treatment, it is effective to add a cation trapping agent such as anisole, phenol, thioanisole, m-cresol, p-cresol, dimethylsulfide, 1,4-butanedithiol or 1,2-ethanedithiol. The 2,4-dinitrophenyl group used as the protective group for the imidazole ring of histidine is eliminated by thiophenol treatment. The formyl group used as the protective group for the indole ring of tryptophan may also be eliminated by alkali treatment using dilute sodium hydroxide, dilute ammonia or the like, as well as the above-mentioned acid treatment in the presence of 1,2-ethanedithiol, 1,4-butanedithiol or the like.

After completion of the reaction, the cyclic pentapeptide represented by formula [I] thus produced is collected by separation methods for peptides such as extraction, distribution, reprecipitation, recrystallization, column chromatography and high performance liquid chromatography.

The cyclic pentapeptides according to the present invention represented by formula [I] can also be obtained by known methods as the salts such as the sodium salt, the potassium salt, the calcium salt and the magnesium salt, and the acid addition salts, particularly the pharmaceutically acceptable acid addition salts. Examples of such salts include the salts of inorganic acids (for example, hydrochloric acid, sulfuric acid and phosphoric acid) and organic acids (for example, acetic acid, propionic acid, citric acid, tartaric acid, malic acid, oxalic acid and methanesulfonic acid).

Now, the three-dimensional structure of the cyclic pentapeptides obtained according to the present invention will be described.

The technique for three-dimensioanl structure analysis used in the present invention is based on the pulse-Fourier transform two-dimensional NMR pioneered by Ernst (who won the Nobel Prize for Chemistry in 1991) and developed for determining the conformation of biopolymers in solutions by Wüthrich et al. The number of peptides and proteins whose three-dimensional structure have been determined by this technique amounts to several hundreds to date. This technique is a main process for determining the three-dimensional structure, as well as X-ray crystallography.

(1) Three-Dimensional Structure of Cyclic Pentapeptide Cyclo(-D-Glu-Ala-D-Phe-Leu-D-Trp-) (A)

Figure 1:
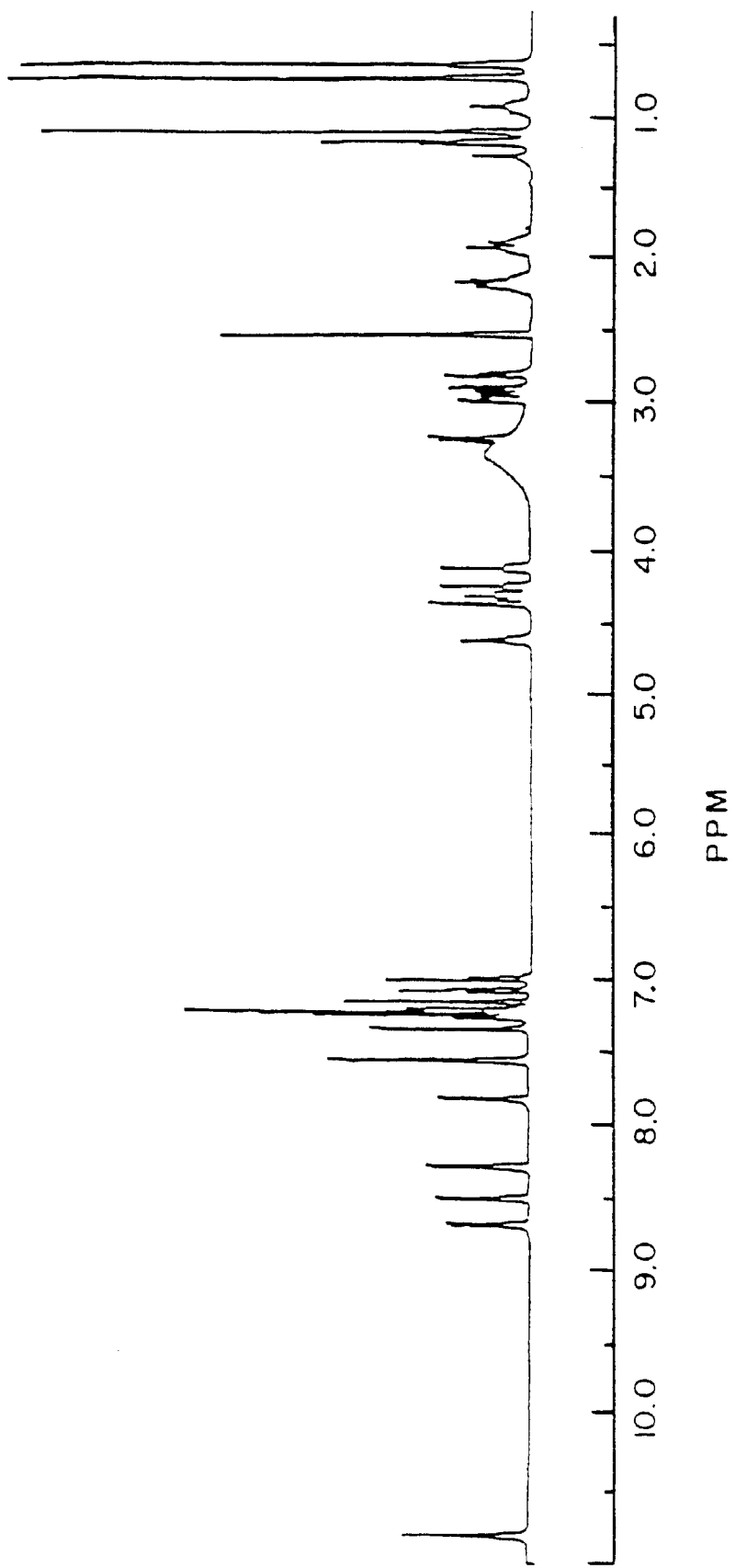
FIG. 1 shows a $^1$H NMR spectrum of cyclic pentapeptide cyclo(-D-Glu-Ala-D-Phe-Leu-D-Trp-) (A).
Figure 2:
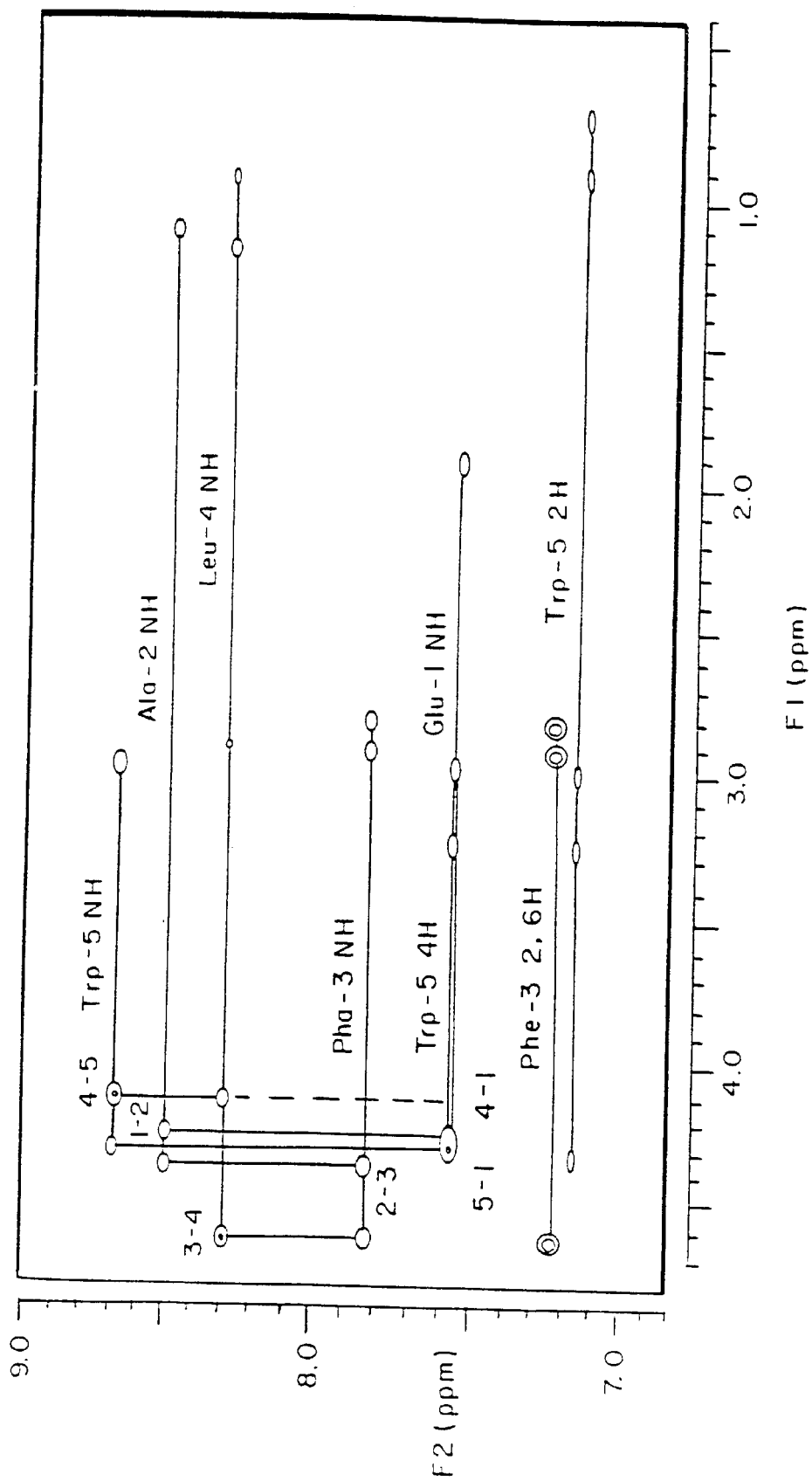
FIG. 2 shows a ROESY spectrum ($\tau_m$=120 ms) of cyclic pentapeptide (A). The horizontal lines each indicate correlations with protons described in the drawing, and the numerals with hyphens indicate sequential connectivity between i-th α-protons and (i+1)-th amide protons.

Cyclic pentapeptide (A) produced by the above-mentioned method (the details are described in Example 1 given later) was dissolved in dimethylsulfoxide(DMSO)-$d_6$ at a concentration of 6.7 mg/ml to prepare a sample for NMR, and the measurement was conducted with an AM500 spectrometer (Bruker) in the following manner. Signal separation was examined according to a one-dimensional $^1$H NMR spectrum at 30° C. (FIG. 1), and then, DQF-COSY (double-quantum filtered correlation spectroscopy), HOHAHA (homonuclear Hartmann-Hahn spectroscopy) ($\tau_{mix}$=90 ms) and ROESY (rotating frame Overhanser affect spectroscopy) ($\tau_{mix}$=20, 40, 60, 80, 100, 120 ms) spectra were measured by the technique of Wüthrich et al. [K. Wüthrich, *NMR of Proteins and Nucleic Acids*, Wiley, New York (1986)], followed by assignment of each proton signal through a sequential assignment procedure (FIG. 2). The range of dihedral angles $\phi$ and $\chi^1$ was restrained by $J_{NH\_\alpha H}$ and $J\alpha H\_\beta H$ values, in addition to distance constraints collected from ROESY. The temperature dependence of amide protons was examined to determine the presence or absence of intramolecular hydrogen bonds, though not employed as distance constraints. FIG. 3 shows a summary of the NMR information described above. Distance geometry calculations were conducted using the resulting distance information, and distance-restrained energy minimization were further conducted to determine the three-dimensional structure of FIG. 4.

Charactristics from the conformational point of view were a $\gamma$-turn found in positions 1-2-3 and a $\beta$-turn in positions 3-4-5-1 of the main chain. Hydrogen bonds were formed between the amide proton of position 3 and carbonyl oxygen of position 1, and between the amide proton of position 1 and carbonyl oxygen of position 3, which is consistent with the low temperature dependence of amide protons in the 1- and 3-positions.

(2) Three-Dimensional Structure of Cyclic Pentapeptide Cyclo(-Trp-D-Leu-Leu-D-Ala-Glu-) (B)

Retro-inverso form (B) was designed and synthesized according to the above-mentioned method with the expectation that it would adopt a similar conformation to and the same arrangement of side chains with that of cyclo(-D-Glu-Ala-D-Leu-Leu-D-Trp-) (C) having the same main chain conformation as pentapeptide (A). A "retro-inverso form" means a peptide in which the sequence of amino acid residues and the arrangement of D and L are reversed. As is shown in FIG. 5, retro-inverso form (B) was expected to have the similar main chain conformation and arrangement of side chains as (C), only with the exception that the amino groups and the carbonyl groups were exchanged for each other in (C). In this case, retro-inverso form (B) has a $\beta$-turn structure in positions 5-1-2-3 and a $\gamma$-turn structure in positions 3-4-5, and hydrogen bonds are formed between the amide proton of position 5 and carbonyl oxygen of position 3 and between the amide proton of position 3 and carbonyl oxygen of position 5.

Retro-inverso form (B) was dissolved in DMSO-$d_6$ at a concentration of 5.5 mg/ml to prepare a sample for NMR, and signal separation was examined according to a one-dimensional $^1$H NMR spectrum at 30° C. (FIG. 6), followed by measurement of DQF-COSY, HOHAHA ($\tau_{mix}$=90 ms) and ROESY ($\tau_{mix}$=30, 60, 90, 120 ms) spectra. Each proton signal was assigned by a sequential assignment procedure (FIG. 7). In a manner similar to that of (1), restraints for dihedral angles $\phi$ and $\chi^1$ and distance constraints were collected from $J_{NH\_\alpha H}$ and $J\alpha H\_\beta H$ values and ROESY and the temperature dependence of amide protons were examined (FIG. 8). Calculations were carried out with the resulting distance information as in the case of (A) to determine the three-dimensional structure of FIG. 9.

The resulting three-dimensional structure was different from the expected one. Namely, a $\gamma$-turn was formed in positions 1-2-3, a $\beta$-turn of type II was formed in positions 3-4-5-1, and hydrogen bonds were formed between the amide proton of position 3 and carbonyl oxygen of position 1 and between the amide proton of position 1 and carbonyl oxygen of position 3, which is consistent with temperature dependence.

(3) Law Derived from Three-Dimensional Structure of (A) and (B)

Cyclo(-Glu-D-Ala-Phe-D-Leu-Trp-) (A') obtained by exchanging the arrangement of D and L in (A) should have the conformation enantiomeric of (A) as shown in FIG. 10. Results of this analysis revealed that (B) had the same main chain conformation as (A'). Although the kinds of side chains of (B) are entirely different from those of (A') in the corresponding positions, (B) has the same main chain conformation as (A'). It is concluded from this observation that the main chain conformation is determined by the arrangement of D and L. That is, each of the cyclic pentapeptides having arrangements -L-D-L-D-L- and -D-L-D-L-D- will form a $\gamma$-turn in positions 1-2-3 and a $\beta$-turn of type II in positions 3-4-5-1, regardless of the kinds of side chains.

According to the manufacturing method of the present invention, compounds having a three-dimensional structure of $\beta$-turns and $\gamma$-turns can be synthesized, regardless of the kinds of amino acid residues, and it is possible to synthesize compounds in which desired amino acid residues are introduced into sites of $\beta$-turn and $\gamma$-turn based on their importance from the viewpoint of biological activity. The present invention is therefore useful for design of a variety compounds having biological activity.

The cyclic pentapeptides of the present invention have a rigid conformation because of the presence of a $\beta$-turn in combination with a $\gamma$-turn and have ability to bind to a specific structural receptor based on the specific amino acid residues of the peptide design. Therefore, they are available for screening a receptor and determining a structure and function of the receptor and they may be some antagonists or agonists through the relationship with the receptors.

In particular, the specific cyclic pentapeptides of Formula I produced by the present invention show, for example, pharmacologic action such as antagonist against NK2 receptor or endothelin receptor, and are useful as drugs such as an antiasthmatic agent, an anti-inflammatory agent or an antarthritics.

The cyclic pentapeptides of the present invention may be used as a reagent for assay of the reactive selectivity on NK2 receptor or endothelin A or B receptor of sample cells or tissues.

The cyclic pentapeptides of the present invention may be used as a purification agent by affinitiy column chromatography.

The cyclic peptides [I] of the present invention have the remarkable activity of suppressing the smooth muscle contraction through NK2 receptors and has low toxicity. For this reason, the cyclic peptides of the present invention or the salts thereof can be used as prophylactic and therapeutic drugs as NK2 receptor antagonist, for example, an anti-asthmatic agent, an anti-inflammatory agents and antarthritics for mammals such as mouse, rat, rabbit, cat, dog, monkey and man.

The cyclic peptides of the present invention, when used as the above-mentioned prophylactic and therapeutic drugs, can be safely administered orally or parenterally in the form of powders, granules, tablets, capsules, injections, suppositories, ointments or sustained release preparations, alone or in combination with pharmaceutically acceptable carriers, excipients or diluents, such as an aqueous solvent (eg. distilled water, physiological saline, Ringer's solution), isotonic agents (eg. glucose, D-sorbitol, D-mannitol, sodium chloride), antiseptics (eg. benzyl alcohol, chlorobutanol, methyl paraoxybenzoate, propyl paraoxybenzoate), buffers (eg. phosphate buffer, sodium acetate buffer). The peptides of the present invention are typically administered parenterally, for example, by intravenous or subcutaneous injection, intraventricular or intraspinal administration, nasotracheal administration or intrarectal administration. In some cases, however, they are administered orally.

The cyclic peptides of the present invention are generally stable substances, and therefore, can be stored as physiological saline solutions. It is also possible to lyophilize the peptides, store them in ampules with mannitol or sorbitol, and dissolve them in a suitable carrier at the time of use. The cyclic peptides of the present invention can be given in their free forms, or in the form of base salts or acid addition salts thereof. All of the free cyclic peptides, the base salts and the acid addition salts thereof are generally given in a proper dose (one dose) within the range of 1 $\mu$g to 100 mg of free peptide per kg of weight. More specifically, although the dosage varies depending on the type of disease to be treated, the symptom of the disease, the object to which the drugs are given and the route of administration, when given by injection to adult patients, it is advantageous that the active ingredients (the peptides [I] or pharmaceutically acceptable salt thereof) are normally given in one dose of about 1 $\mu$g to 100 mg/kg of weight, more preferably about 100 $\mu$g to 20 mg/kg of weight, most preferably 1 mg to 20 mg/kg of weight, about once to 3 times a day. In injection, the peptides [I] are usually given intravenously. Drip infusion is also effective. In this case, the total dosage is the same as with injection.

When the cyclic peptides of the present invention or the pharmaceutically acceptable salts thereof are used as the prophylactic or therapeutic drugs, they must be carefully purified so as to contain no bacteria and no pyrogens.

EXAMPLES

The present invention will be described in more detail with the following examples, in which all amino acid residues take the L-form unless otherwise specified, when they have the D- and L-forms.

In the following examples, SILICAGEL 60F-254 (Merck) was used as plates of thin layer chromatography, and chloroform-methanol (19:1) and chloroform-methanol-acetic acid (9:1:0.5) were used as developing solvents for $Rf_1$ and $Rf_2$, respectively.

Example 1

Production of Cyclo(-D-Glu-Ala-D-Phe-Leu-D-Trp-)

(I) Production of Boc-Ala-OPac 28.4 g of Boc-Ala-OH and 24.5 g of $Cs_2CO_3$ were dissolved in 90% aqueous MeOH, and the resulting solution was concentrated. The residue was dissolved in 450 ml of DMF, and 32.9 g of phenacyl bromide was added thereto, followed by stirring overnight. The resulting precipitate was separated by filtration, and the filtrate was concentrated to obtain a residue. The residue was dissolved in AcOEt, and the resulting solution was washed with 4% aqueous $NaHCO_3$ and 10% aqueous citric acid. After washing with water, the solution was dried with $Na_2SO_4$ and concentrated. Ether was added to the resulting residue to separate out a precipitate, which was collected by filtration.

Yield: 42.4 g (91.9%)
Melting point: 123° C., $RF_1$: 0.72, $RF_2$: 0.74
$[\alpha]_D^{28}$ −46.1° (c = 1.36, in DMF)
Elemental analysis: As $C_{16}H_{21}NO_5$

| | | | |
|---|---|---|---|
| Calculated: | C, 62.53; | H, 6.89; | N, 4.56 |
| Found: | C, 62.94; | H, 6.87; | N, 4.63 |

(II) Production of Boc-D-Glu(OBzl)-Ala-OPac 2.02 g of Boc-D-Glu(OBzl)-OH was dissolved in THF, and the resulting solution was cooled to −15° C. with stirring. Then, 0.66 ml of N-methylmorpholine was added thereto, and subsequently, 0.80 ml of IBCF was added. After 2 minutes, a DMF solution of HCl.H-Ala-OPac and 0.66 ml of N-methylmorpholine was added. HCl.H-Ala-OPac was obtained by adding 20 ml of TFA to 1.84 g of Boc-Ala-OPac to dissolve it, followed by concentration, adding 1.95 ml of 8 N-HCl/dioxane thereto, and further adding ether to precipitate crystals, which were collected by filtration and dried. After stirring at −15° C. for 30 minutes, the solution was brought to room temperature. After 30 minutes, the resulting insoluble material was separated by filtration, followed by concentration. The residue was dissolved in AcOEt, and the solution was washed with 4% aqueous $NaHCO_3$ and 10% aqueous citric acid. After washing with water, the solution was dried with $Na_2SO_4$ and concentrated. Crystals were collected from AcOEt-petroleum ether by filtration.

Yield: 2.63 g (83.2%)
Melting point: 128° C., $Rf_1$: 0.54, $Rf_2$: 0.65
$[\alpha]_D^{28}$ −13.0° (c = 1.19, in DMF)
Elemental analysis: As $C_{28}H_{34}N_2O_8$

| | | | |
|---|---|---|---|
| Calculated: | C, 63.87; | H, 6.51; | N, 5.32 |
| Found: | C, 63.88; | H, 6.32; | N, 5.18 |

(III) Production of Boc-D-Trp-D-Glu(OBzl)-Ala-OPac 20 ml of TFA was added to 1.05 g of Boc-D-Glu(OBzl)-Ala-OPac to dissolve it, followed by concentration. Then, 0.58 ml of 8 N-HCl/dioxane was added, and ether was added to precipitate crystals, which were separated by filtration and then dried. The resulting product was dissolved in 15 ml of DMF and cooled with ice. Then, 0.20 ml of TEA was added thereto. Boc-D-Trp-ONB (prepared from 0.67 g of Boc-D-Trp-OH, 0.43 g of HONB and 0.50 g of DCC) was added thereto, followed by stirring overnight. The resulting insoluble material was separated by filtration, followed by concentration. The residue was dissolved in AcOEt, and the solution was washed with 4% aqueous $NaHCO_3$ and 10% aqueous citric acid. After washing with water, the solution was dried with $Na_2SO_4$ and concentrated. Ether was added to the resulting residue to separate out a precipitate, which was collected by filtration.

Yield: 1.39 g (97.8%)
Melting point: 127–129° C., $Rf_1$: 0.36, $Rf_2$: 0.62
$[\alpha]_D^{28}$ −4.04° (c = 1.04, in DMF)

Elemental analysis: As $C_{39}H_{44}N_4O_9$

| | | | |
|---|---|---|---|
| Calculated: | C, 65.72; | H, 6.22; | N, 7.86 |
| Found: | C, 65.62; | H, 6.46; | N, 7.78 |

(IV) Production of Boc-Leu-D-Trp-D-Glu(OBzl)-Ala-OPac 21.4 g of Boc-D-Trp-D-Glu(OBzl)-Ala-OPac was suspended in dioxane, and 5.1 ml of ethanedithiol was added thereto, followed by ice cooling. 8-N HCl/dioxane was added thereto, and the solution was stirred under ice cooling for 1 hour, followed by concentration. Ether was added to precipitate crystals, which were separated by filtration and dried. The resulting product was dissolved in 150 ml of DMF and cooled with ice. Then, 8.42 ml of TEA was added thereto. Boc-Leu-ONB (prepared from 8.22 g of Boc-Leu-OH.H$_2$O, 6.51 g of HONB and 7.50 g of DCC) was added thereto, followed by stirring overnight. The resulting insoluble material was separated by filtration, followed by concentration. The residue was dissolved in AcOEt, and the solution was washed with 4% aqueous NaHCO$_3$ and 10% aqueous citric acid. After washing with water, the solution was dried with Na$_2$SO$_4$ and concentrated. Ether was added to the resulting residue to separate out a precipitate, which was collected by filtration.

Yield: 23.0 g (92.8%)
Melting point: 127–128° C., $Rf_1$: 0.35, $Rf_2$: 0.63
$[\alpha]_D^{28}$ −9.91° (c = 1.15, in DMF)

Elemental analysis: As $C_{45}H_{55}N_4O_{10}$

| | | | |
|---|---|---|---|
| Calculated: | C, 65.44; | H, 6.71; | N, 8.48 |
| Found: | C, 65.39; | H, 6.92; | N, 8.30 |

(V) Production of Boc-D-Phe-Leu-D-Trp-D-Glu(OBzl)-Ala-OPac 2.07 g of Boc-Leu-D-Trp-D-Glu(OBzl)-Ala-OPac was suspended in dioxane, and 0.42 ml of ethanedithiol was added thereto, followed by ice cooling. 8-N HCl/dioxane was added thereto, and the solution was stirred under ice cooling for 30 minutes, followed by concentration. Ether was added to precipitate crystals, which were separated by filtration and dried. The resulting product was dissolved in 15 ml of DMF and cooled with ice. Then, 0.70 ml of TEA was added thereto. Thereafter, 0.73 g of Boc-D-Phe-OH, 0.41 g of HOBt and 0.63 g of DCC were added thereto, followed by stirring overnight. The resulting insoluble material was separated by filtration, followed by concentration. The residue was dissolved in AcOEt, and the solution was washed with 4% aqueous NaHCO$_3$ and 10% aqueous citric acid. After washing with water, the solution was dried with Na$_2$SO$_4$ and concentrated. Ether was added to the resulting residue to separate out a precipitate, which was collected by filtration.

Yield: 2.37 g (97.4%)

(VI) Production of Boc-D-Phe-Leu-D-Trp-D-Glu(OBzl)-Ala-OH 1.46 g of Boc-D-Phe-Leu-D-Trp-D-Glu(OBzl)-Ala-OPac was dissolved in 20 ml of 90% aqueous AcOH, and 4.91 g of Zn powder was added thereto, followed by stirring for 3 hours. The Zn powder was separated by filtration, and the filtrate was concentrated. AcOEt was added to the residue to dissolve it, and the solution was washed with 10% aqueous citric acid. After washing with water, the solution was dried with Na$_2$SO$_4$ and concentrated. Ether was added to the resulting residue to separate out a precipitate, which was collected by filtration.

Yield: 1.20 g (93.6%)

(VII) Production of Cyclo(-D-Glu-Ala-D-Phe-Leu-D-Trp-)

0.43 g of Boc-D-Phe-Leu-D-Trp-D-Glu(OBzl)-Ala-OH was dissolved in 20 ml of DCM, and the solution was cooled with ice. Then, 0.18 g of HONB and 0.21 g of DCC were added thereto, followed by stirring for 3 hours. Subsequently, the resulting DCU was separated by filtration, followed by concentration, and ether was added to the residue to separate out a precipitate, which was collected by filtration. Then, 0.09 ml of ethanedithiol and 20 ml of 8-N HCl/dioxane were added thereto under ice cooling to dissolve the precipitate. The resulting solution was stirred for 10 minutes and concentrated. Ether was added to the residue to separate out a precipitate, which was collected by filtration and dried. The precipitate was dissolved in 10 ml of DMF, and the resulting solution was added dropwise to 90 ml of DMF containing 0.7 ml of TEA for 30 minutes, followed by stirring overnight and concentration. Acetonitrile was added to the resulting residue to separate out a precipitate, which was collected by filtration and dried. Of this precipitate, 74 mg was dissolved in 15 ml of DMF, and catalytically reduced in a stream of hydrogen using palladium black as a catalyst. The catalyst was separated by filtration, and the filtrate was concentrated. The resulting residue was dissolved in a small amount of AcOH, and-then, water was added thereto to conduct lyophilization. Finally, the lyophilized product was purified by liquid chromatography using a YMC-D-ODS-5 (purchased from YMC Company Ltd.) column (2 cm×25 cm) (YMC Company Ltd., Japan) to obtain a desired material.

Yield: 9.1 mg (14.1%).

Amino acid ratios (110° C., hydrolysis for 24 hours; figures in parentheses show theoretical values.):

Glu 1.00 (1); Ala 0.98 (1); Leu 0.76 (1); Phe 0.81 (1)
LSIMS (Liquid Secondary Ion Mass Spectrometry) (M+H$^+$)=647, (theoretical value)=647

Example 2

Production of Cyclo(-Trp-D-Leu-Leu-D-Ala-Glu-)

(I) Production of Boc-D-Leu-Leu-OBzl 21.6 g of H-Leu-OBzl Tos was dissolved in 100 ml of DMF, and the solution was cooled with ice. Then, 7.7 ml of TEA and Boc-D-Leu-ONB (prepared from 12.5 g of Boc-D-Leu-OH.H$_2$O, 9.86 g of HONB and 11.4 g of DCC) were added thereto, followed by stirring overnight. Subsequently, the resulting DCU was separated by filtration, and the filtrate was concentrated. The residue was dissolved in AcOEt, and the solution was washed with 4% aqueous NaHCO$_3$ and 10% aqueous citric acid. After washing with water, the solution was dried with Na$_2$SO$_4$ and concentrated. Ether was added to the resulting residue to separate out a precipitate, which was collected by filtration.

Yield: 19.8 g (91.3%)
Melting point: 94–95° C., $Rf_2$: 0.76
$[\alpha]_D^{25}$ +3.6° (c = 1.06, in DMF)

Elemental analysis: As $C_{24}H_{38}N_2O_5$

| | | | |
|---|---|---|---|
| Calculated: | C, 66.33; | H, 8.81; | N, 6.45 |
| Found: | C, 66.38; | H, 8.87; | N, 6.53 |

(II) Production of Boc-D-Leu-Leu-OPac 6.0 g of Boc-D-Leu-Leu-OBzl was dissolved in 20 ml of methanol and catalytically reduced in a stream of hydrogen using 10% Pd-carbon as a catalyst. After the catalyst was separated by filtration, the solution was concentrated to obtain a residue. The residue and 2.1 g of $Cs_2CO_3$ were dissolved in 90% aqueous methanol, and the solution was concentrated. The resulting residue was dissolved in 60 ml of DMF, and 2.8 g of phenacyl bromide was added thereto, followed by stirring overnight. The resulting precipitate was separated by filtration, and the filtrate was concentrated to obtain a residue. The residue was dissolved in AcOEt, and the resulting solution was washed with 4% aqueous $NaHCO_3$ and 10% aqueous citric acid. After washing with water, the solution was dried with $Na_2SO_4$ and concentrated. Ether was added to the resulting residue to separate out a precipitate, which was collected by filtration.

Yield: 5.48 g (85.8%)
Melting point: 98–99° C., $Rf_2$: 0.66
$[\alpha]_D^{25}$ −3.9° (c = 1.09, in DMF)
Elemental analysis: As $C_{25}H_{38}N_2O_6$

|  | | | |
|---|---|---|---|
| Calculated: | C, 64.91; | H, 8.28; | N, 6.06 |
| Found: | C, 65.21; | H, 8.54; | N, 6.24 |

(III) Production of Boc-Trp-D-Leu-Leu-OPac 9.25 g of Boc-D-Leu-Leu-OPac was dissolved in 5.0 ml of dioxane, and the solution was cooled with ice. Then, 30.0 ml of 10 N-HCl/dioxane was added thereto, followed by stirring for 30 minutes. The solvent was removed by distillation at room temperature, and dried under reduced pressure. The resulting product was dissolved in 20 ml of DMF, and neutralized with TEA with stirring under ice cooling. Boc-Trp-ONB (prepared from 6.08 g of Boc-Trp-OH, 4.30 g of HONB and 5.45 g of DCC) was added thereto and stirred overnight at room temperature. The resulting insoluble material was removed by filtration, and the filtrate was concentrated. The residue was dissolved in ethyl acetate, and the solution was washed with 4% aqueous sodium bicarbonate and 10% aqueous citric acid. After washing with water, the solution was dried with $Na_2SO_4$ and concentrated. Ether-petroleum ether was added to the residue to separate out a precipitate, which was collected by filtration.

Yield: 12.19 g (93.9%)
Melting point: 98–100° C., $Rf_1$: 0.43, $Rf_2$: 0.67
Elemental analysis: As $C_{36}H_{48}N_4O_7$

|  | | | |
|---|---|---|---|
| Calculated: | C, 66.65; | H, 7.46; | N, 8.64 |
| Found: | C, 66.73; | H, 7.41; | N, 8.45 |

(IV) Production of Boc-Glu(OBzl)-Trp-D-Leu-Leu-OPac 3.24 g of Boc-Trp-D-Leu-Leu-OPac was dissolved in 2.0 ml of dioxane, and the solution was cooled with ice. Then, 10.0 ml of 10 N-HCl/dioxane was added thereto, followed by stirring for 30 minutes. The solvent was removed by distillation at room temperature, and ether was added to the residue to separate out a precipitate, which was collected by filtration and dried under reduced pressure. The resulting product was dissolved in 10 ml of DMF, and neutralized with TEA with stirring under ice cooling. Boc-Glu(OBzl)-ONB (prepared from 1.78 g of Boc-Glu(OBzl)-OH, 1.18 g of HONB and 1.36 g of DCC) was added thereto and stirred overnight at room temperature. The resulting insoluble material was removed by filtration, and the filtrate was concentrated. The residue was dissolved in ethyl acetate, and the solution was washed with 4% aqueous sodium bicarbonate and 10% aqueous citric acid. After washing with water, the solution was dried with $Na_2SO_4$ and concentrated. Ether-petroleum ether was added to the residue to separate out a precipitate, which was collected by filtration.

Yield: 3.91 g (87.2%)
Melting point: 88–90° C., $Rf_1$: 0.37, $Rf_2$: 0.67
Elemental analysis: As $C_{48}H_{65}N_5O_{12}$

|  | | | |
|---|---|---|---|
| Calculated: | C, 63.77; | H, 7.25; | N, 7.75 |
| Found: | C, 63.93; | H, 7.33; | N, 7.57 |

(V) Production of Boc-D-Ala-Glu(OBzl)-Trp-D-Leu-Leu-OPac 3.14 g of Boc-Glu(OBzl)-Trp-D-Leu-Leu-OPac was dissolved in 2.0 ml of dioxane, and the solution was cooled with ice. Then, 10.0 ml of 10 N-HCl/dioxane was added thereto, followed by stirring for 30 minutes. The solvent was removed by distillation at room temperature, and ether was added to the residue to separate out a precipitate, which was collected by filtration and dried under reduced pressure. The resulting product was dissolved in 10 ml of DMF, and neutralized with TEA with stirring under ice cooling. Boc-D-Ala-ONB (prepared from 0.83 g of Boc-D-Ala-OH, 0.86 g of HONB and 1.16 g of DCC) was added thereto and stirred overnight at room temperature. The resulting insoluble material was removed by filtration, and the filtrate was concentrated. The residue was dissolved in ethyl acetate, and the solution was washed with 4% aqueous sodium bicarbonate and 10% aqueous citric acid. After washing with water, the solution was dried with $Na_2SO_4$ and concentrated. Ether-petroleum ether was added to the residue to separate out a precipitate, which was collected by filtration.

Yield: 2.94 g (89.5%)
Melting point: 188–190° C., $Rf_1$: 0.29, $Rf_2$: 0.67
Elemental analysis: As $C_{51}H_{66}N_6O_{11}$

|  | | | |
|---|---|---|---|
| Calculated: | C, 65.23; | H, 7.08; | N, 8.95 |
| Found: | C, 65.98; | H, 7.23; | N, 8.87 |

(VI) Production of Boc-D-Ala-Glu(OBzl)-Trp-D-Leu-Leu-OH 1.41 g of Boc-D-Ala-Glu(OBzl)-Trp-D-Leu-Leu-OPac was dissolved in 50 ml of 90% aqueous acetic acid, and 4.96 g of Zn powder was added thereto with stirring under ice cooling, further followed by stirring at room temperature for 4 hours. The Zn powder was removed by filtration, and the filtrate was concentrated. The residue was dissolved in ethyl acetate, and the solution was washed successively with 10% aqueous citric acid and a saturated aqueous solution of sodium chloride. After drying with $Na_2SO_4$, the solvent was removed by distillation, and ether-petroleum ether was added to the residue to separate out a precipitate, which was collected by filtration. Then, the resulting product was dried under reduced pressure.

Yield: 1.05 g (85.8%) Melting point: 122.0-124.0° C., $Rf_1$: 0.06, $Rf_2$: 0.56

(VII) Production of Cyclo(-Trp-D-Leu-Leu-D-Ala-Glu(OBzl)-)

0.30 g of Boc-D-Ala-Glu(OBzl)-Trp-D-Leu-Leu-OH was dissolved in 3.5 ml of dichloromethane, and 143 mg of HONB and 165 mg of DCC were successively added thereto with stirring under ice cooling, further followed by stirring under ice cooling for 3 hours. The resulting insoluble material was removed by filtration, and the solvent was removed by distillation. Acetonitrile was added to the residue to separate out a precipitate, which was collected by filtration and dried under reduced pressure. The resulting product was dissolved in 2 ml of dioxane, and 10 ml of 10 N-HCl/dioxane was added thereto with stirring under ice cooling, further followed by stirring for 10 minutes. The solvent was removed by distillation at room temperature, and ether was added to the residue to separate out a precipitate, which was collected by filtration and dried under reduced pressure. This product was dissolved in 5 ml of DMF, and the resulting solution was added dropwise to 80 ml of DMF containing 5.57 ml of TEA, further followed by stirring overnight. The solvent was removed by distillation, and the residue was dissolved in a small amount of DMF. Then, ethyl acetate was added thereto to separate out a precipitate, which was collected by filtration and dried under reduced pressure.

Yield: 195 mg (75.9%), $Rf_1$: 0.29, $Rf_2$: 0.67

(VIII) Production of Cyclo(-Trp-D-Leu-Leu-D-Ala-Glu-)

100 mg of cyclo(-Trp-D-Leu-Leu-D-Ala-Glu(OBzl)-) was dissolved in 10 ml of DMF, and 100 mg of Pd black was added thereto. The mixture was vigorously stirred in a stream of hydrogen at room temperature for 1 hour. The catalyst was removed by filtration, and the filtrate was concentrated. Then, ether was added to the residue to separate out a precipitate, which was collected by filtration and dried under reduced pressure.

Yield: 85 mg (98.0%).

Of this, 30.0 mg was purified by reversed phase liquid chromatography [column: YMC-D-ODS-5 (2 cm×25 cm), solvent: 40% acetonitrile/$H_2O$ (0.1% TFA)].

Yield: 22.5 mg

Amino acid ratios (6 N-HCl, 110° C., hydrolysis for 24 hours; figures in parentheses show theoretical values.): Ala 1.05 (1); Glu 1.08 (1); Leu 2.20 (2)

LSIMS $(M+H^+)$=613, (theoretical value)=613

Example 3

Production of Cyclo(-D-Glu-Ser(Bzl)-D-Leu-Leu-D-Trp-)

The above-mentioned cyclic peptide was synthesized in a manner similar to that of Example 2 except for that Boc-Ser(Bzl)-OH, Boc-D-Glu(OBzl)-OH and Boc-D-Trp-OH were used respectively in place of Boc-Trp-OH, Boc-Glu(OBzl)-OH and Boc-D-Ala-OH.

LSIMS $(M+H^+)$=719, (theoretical value)=719

Example 4

Production of Cyclo(-D-Glu-Thr(Bzl)-D-Leu-Leu-D-Trp-)

The above-mentioned cyclic peptide was synthesized in a manner similar to that of Example 2 except for that Boc-Thr(Bzl)-OH, Boc-D-Glu(OBzl)-OH and Boc-D-Trp-OH were used respectively in place of Boc-Trp-OH, Boc-Glu(OBzl)-OH and Boc-D-Ala-OH.

LSIMS $(M+H^+)$=733, (theoretical value)=733

Example 5

Production of Cyclo(-D-Asp-Trp-D-Leu-Leu-D-Trp-)

The above-mentioned cyclic peptide was synthesized in a manner similar to that of Example 2 except for that Boc-D-Asp(OBzl)-OH and Boc-D-Trp-OH were used respectively in place of Boc-Glu(OBzl)-OH and Boc-D-Ala-OH.

LSIMS $(M+H^+)$=714, (theoretical value)=714

Experimental Example 1

Assay of Affinity for Receptor . . . Binding Inhibiting Activity on NK2 Receptor The method of Paul L. M. Van Giersbergen et al. [*Proc. Natl. Acad. Sci. U.S.A.*, 88, 1661 (1991)] was modified for this assay. The membrane fraction containing the receptor was prepared from the inner wall of the bovine third stomach (purchased from Kyoto Chuo Chikusan Fukuseibutsu Oroshi Kyokai).

The inner wall of the bovine third stomach stored at −80° C. was cut to 1 cm×1 cm or less, and disrupted in 3 liters/kg of 50 mM Tris-HCl buffer (pH 7.4) supplemented with 120 mM sodium chloride, 5 mM potassium chloride, 0.02% BSA and 5% sucrose, using a polytron homogenizer (Kinematika, Germany). Then, the disrupted product was centrifuged at 1,000×g for 10 minutes. The supernatant was further centrifuged at 45,000×g for 20 minutes. The precipitate was suspended in 200 ml of 50 mM Tris-HCl buffer (pH 7.4) supplemented with 300 mM potassium chloride, 10 mM ethylenediaminetetraacetic acid, 0.1 mM phenylmethylsulfonium fluoride and 0.02% BSA, and gently stirred under ice cooling for 60 minutes. The suspension was centrifuged at 45,000×g for 20 minutes. The precipitate was washed with 200 ml of 50 mM Tris-HCl buffer (pH 7.4), and stored in the frozen state at −40° C. as a receptor sample.

This sample was suspended in a reaction buffer solution [50 mM Tris-HCl buffer (pH 7.4), 0.02% bovine serum albumin and 4 mM manganese chloride] so as to give a protein concentration of 0.7 mg/ml, and 100 μl thereof was used for reaction. A test sample and $^{125}$I-NKA (0.61 KBq, $^{125}$I-neurokinin A, 81.4 TBq/mmol, Du Pont/NEN Research Products, U.S.A.) were also added, and reacted in 0.2 ml of the reaction buffer solution at 25° C. for 3 hours. The reaction mixture was rapidly filtered through a glass filter (GF/B, Whatman, U.S.A.) using a cell harvester (Type 290PHD, Cambridge Technology Inc., U.S.A.) to terminate the reaction, and washed 3 times with 250 μl of 50 mM Tris-HCl buffer (pH 7.4) supplemented with 0.02% bovine serum albumin. The radioactivity left on the filter was measured with a gamma-ray counter. Results are shown in Table 1 as binding inhibiting activity ($IC_{50}$, unit: μM) on the NK2 receptor.

TABLE 1

| Binding Inhibiting Activity on NK2 Receptor | |
| --- | --- |
| Compound | $IC_{50}$ (μM) |
| Cyclo(-D-Glu-Ser(Bzl)-D-Leu-Leu-D-Trp-) | 0.58 |
| Cyclo(-D-Glu-Thr(Bzl)-D-Leu-Leu-D-Trp-) | 1.5 |
| Cyclo(-D-Asp-Trp-D-Leu-Leu-D-Trp-) | 0.027 |

What is claimed is:

1. A method for synthesizing a cyclopentapeptide compound, having a β-turn and γ-turn with a main chain configuration of:

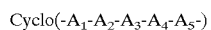

wherein each of $A_1$, $A_3$ to $A_5$ is an a-amino acid selected from alanine, valine, norvaline, leucine, norleucine, isoleucine, alloisoleucine, phenylalanine, tyrosine, tryptophan, serine, threonine, aspartic acid, glutamic acid, ornithine, lysine, arginine, histidine, methionine and cysteine; and $A_2$ is an α-amino acid selected from alanine, valine, norvaline, leucine, norleucine, isoleucine, alloisoleucine, phenylalanine, tyrosine, tryptophan, serine, threonine, aspartic acid, glutamic acid, ornithine, lysine, arginine, histidine, methionine, cysteine and proline, said method comprising the steps of:
(a) providing a D-α-amino acid for each $A_1$, $A_3$ and $A_5$ and providing a L-α-amino acid for each $A_2$ and $A_4$;

(b) synthesizing a linear pentapeptide constituting a precursor of said cyclopentapeptide, and
(c) cyclizing said linear pentapeptide;
thereby forming a β-turn at the portion of $-A_3-A_4-A_5-A_1$ and a γ-turn at the portion of $-A_1-A_2-A_3-$ in said cyclopentapeptide and controlling the optical activity of the main chain of the cyclic pentapeptide, with the proviso that Cyclo ($-A_1-A_2-A_3-A_4-A_5-$) is not Cyclo (-Asp-Pro-Val-Leu-Trp-), Cyclo (-Glu-Ala-Val-Leu-Trp-) and Cyclo (-Glu-Ala-alloIle-Leu-Trp-).

* * * * *